(12) United States Patent
White et al.

(10) Patent No.: US 11,096,685 B2
(45) Date of Patent: Aug. 24, 2021

(54) SURGICAL STAPLER AND FEEDER BELT CONFIGURATIONS

(71) Applicant: Aesculap AG, Tuttlingen (DE)

(72) Inventors: Nathan H. White, Longmont, CO (US); Michael P. Schaller, Palo Alto, CA (US); Michael Murillo, Palo Alto, CA (US); Jared L. Van Cleave, Menlo Park, CA (US); Philipe R. Manoux, Oakland, CA (US); Bryan D. Knodel, Flagstaff, AZ (US); Benjamin J. Matthias, San Mateo, CA (US); John E. Rivera, Woodside, CA (US)

(73) Assignee: AESCULAP AG, Tuttlingen (DE)

( * ) Notice: Subject to any disclaimer, the term of this patent is extended or adjusted under 35 U.S.C. 154(b) by 316 days.

(21) Appl. No.: 16/167,065

(22) Filed: Oct. 22, 2018

(65) Prior Publication Data

US 2019/0053802 A1 Feb. 21, 2019

Related U.S. Application Data

(60) Division of application No. 14/339,054, filed on Jul. 23, 2014, now Pat. No. 10,130,362, which is a
(Continued)

(51) Int. Cl.
| | |
|---|---|
| *A61B 17/068* | (2006.01) |
| *A61B 17/072* | (2006.01) |
| *A61B 17/064* | (2006.01) |
| *A61B 90/00* | (2016.01) |

(52) U.S. Cl.
CPC ...... *A61B 17/07207* (2013.01); *A61B 17/068* (2013.01); *A61B 17/0644* (2013.01);
(Continued)

(58) Field of Classification Search
CPC .......... A61B 2017/07242; A61B 2017/07264; A61B 17/07207; A61B 17/068; A61B 2090/037
See application file for complete search history.

(56) References Cited

U.S. PATENT DOCUMENTS

| | | | |
|---|---|---|---|
| 3,581,551 A | 6/1971 | Wilkinson | |
| 3,650,453 A | 3/1972 | Smith | |
| (Continued) | | | |

FOREIGN PATENT DOCUMENTS

| | | |
|---|---|---|
| EP | 1238634 A2 | 9/2002 |
| EP | 1464287 A2 | 10/2004 |
| (Continued) | | |

OTHER PUBLICATIONS

Cardica Microcutter Implant Delivery Device 510(k), Cover Sheet, Table 10.1, "Substantial Equivalence Comparison", and Section 12, "Substantial Equivalence Discussion".
(Continued)

*Primary Examiner* — Andrew M Tecco

(57) ABSTRACT

A surgical apparatus comprises a surgical staple for treating tissues of a patient in a surgical procedure. The surgical staple is deformable from a first configuration (e.g., an un-deployed configuration) to a second configuration (e.g., a deployed configuration) in accordance with embodiments of the present invention. The surgical staple includes a first leg and a second leg, wherein said surgical staple substantially resembles a V-shape or a suture needle in the first configuration and substantially forms a D-shape in the second configuration in accordance with embodiments of the present invention.

20 Claims, 14 Drawing Sheets

Related U.S. Application Data continuation of application No. 13/746,449, filed on Jan. 22, 2013, now Pat. No. 9,386,986, which is a continuation of application No. 13/282,759, filed on Oct. 27, 2011, now abandoned, which is a division of application No. 12/477,834, filed on Jun. 3, 2009, now Pat. No. 8,056,789, said application No. 13/746,449 is a continuation of application No. 13/090,168, filed on Apr. 19, 2011, now Pat. No. 8,365,973, which is a continuation of application No. 12/477,834, filed on Jun. 3, 2009, now Pat. No. 8,056,789.

(52) U.S. Cl.
CPC ............. *A61B 2017/07228* (2013.01); *A61B 2017/07264* (2013.01); *A61B 2017/07271* (2013.01); *A61B 2017/07278* (2013.01); *A61B 2090/037* (2016.02)

(56) References Cited

U.S. PATENT DOCUMENTS

| | | | |
|---|---|---|---|
| 3,899,914 A | 8/1975 | Akiyama | |
| 4,086,926 A | 5/1978 | Green et al. | |
| 4,179,057 A | 12/1979 | Becht et al. | |
| 4,228,895 A | 10/1980 | Larkin | |
| 4,375,866 A | 3/1983 | Giersch et al. | |
| 4,391,402 A | 7/1983 | Campbell et al. | |
| 4,475,679 A | 10/1984 | Fleury | |
| 4,556,058 A | 12/1985 | Green | |
| 4,573,625 A | 3/1986 | Olesen et al. | |
| 4,583,276 A | 4/1986 | Olesen | |
| 4,589,416 A | 5/1986 | Green | |
| 4,633,861 A | 1/1987 | Chow et al. | |
| 4,762,260 A | 8/1988 | Richards et al. | |
| 4,807,628 A | 2/1989 | Peters et al. | |
| 4,874,122 A | 10/1989 | Froelich et al. | |
| 4,951,860 A | 8/1990 | Peters et al. | |
| 4,969,591 A | 11/1990 | Richards et al. | |
| 4,991,763 A | 2/1991 | Storace | |
| 4,996,820 A | 3/1991 | Harrison | |
| 5,027,834 A | 7/1991 | Pruitt | |
| 5,114,065 A | 5/1992 | Storace | |
| 5,156,315 A | 10/1992 | Green et al. | |
| 5,192,288 A | 3/1993 | Thompson et al. | |
| 5,221,036 A | 6/1993 | Takase | |
| 5,356,064 A | 10/1994 | Green et al. | |
| 5,392,978 A | 2/1995 | Velez et al. | |
| 5,413,272 A | 5/1995 | Green et al. | |
| 5,470,010 A | 11/1995 | Rothfuss et al. | |
| 5,476,206 A | 12/1995 | Green et al. | |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,833,695 A | 11/1998 | Yoon | |
| 5,855,311 A | 1/1999 | Hamblin et al. | |
| 5,894,979 A | 4/1999 | Powell | |
| 5,918,791 A | 7/1999 | Sorrentino et al. | |
| 5,964,774 A | 10/1999 | McKean et al. | |
| 6,306,149 B1 | 10/2001 | Meade et al. | |
| 6,391,038 B2 | 5/2002 | Vargas et al. | |
| 6,602,252 B2 | 8/2003 | Mollenauer | |
| 6,716,232 B1 | 4/2004 | Vidal et al. | |
| 6,817,508 B1 | 11/2004 | Racenet et al. | |
| 6,843,403 B2 | 1/2005 | Whitman | |
| 6,939,358 B2 | 9/2005 | Palacios et al. | |
| 6,994,714 B2 | 2/2006 | Vargas et al. | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,407,077 B2 | 8/2008 | Ortiz et al. | |
| 7,467,740 B2 | 12/2008 | Shelton et al. | |
| 7,481,347 B2 | 1/2009 | Roy | |
| 7,517,356 B2 | 4/2009 | Heinrich | |
| 7,631,793 B2 | 12/2009 | Rethy et al. | |
| 7,686,200 B2 | 3/2010 | Peterson | |
| 7,726,537 B2 | 6/2010 | Olson et al. | |
| 7,837,079 B2 | 11/2010 | Holsten et al. | |
| 7,896,895 B2 | 3/2011 | Boudreaux et al. | |
| 7,918,376 B1 | 4/2011 | Knodel et al. | |
| 7,918,873 B2 | 4/2011 | Cummins | |
| 7,934,630 B2 | 5/2011 | Shelton et al. | |
| 7,934,631 B2 | 5/2011 | Balbierz et al. | |
| 7,963,432 B2 | 6/2011 | Knodel et al. | |
| 7,988,026 B2* | 8/2011 | Knodel ............... | A61B 17/1222 227/175.1 |
| 8,205,780 B2 | 6/2012 | Sorrentino et al. | |
| 8,220,690 B2 | 7/2012 | Hess et al. | |
| 8,365,973 B1 | 2/2013 | White et al. | |
| 8,365,976 B2 | 2/2013 | Hess et al. | |
| 8,403,956 B1 | 3/2013 | Thompson et al. | |
| 8,439,244 B2 | 5/2013 | Holcomb et al. | |
| 8,727,197 B2* | 5/2014 | Hess .................. | A61B 17/0686 227/176.1 |
| 2003/0120284 A1 | 6/2003 | Palacios et al. | |
| 2003/0236551 A1 | 12/2003 | Peterson | |
| 2005/0184121 A1 | 8/2005 | Heinrich et al. | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton et al. | |
| 2007/0194079 A1* | 8/2007 | Hueil ................. | A61B 17/115 227/176.1 |
| 2008/0078802 A1 | 4/2008 | Hess et al. | |
| 2008/0078807 A1* | 4/2008 | Hess .................. | A61B 17/072 227/181.1 |
| 2008/0078808 A1 | 4/2008 | Hess et al. | |
| 2008/0210738 A1 | 9/2008 | Shelton et al. | |
| 2009/0065552 A1* | 3/2009 | Knodel ............... | A61B 17/115 227/180.1 |
| 2009/0255974 A1* | 10/2009 | Viola ................ | A61B 17/07207 227/176.1 |
| 2010/0230464 A1 | 9/2010 | Knodel et al. | |
| 2011/0278343 A1 | 11/2011 | Knodel et al. | |
| 2012/0080497 A1 | 4/2012 | White et al. | |

FOREIGN PATENT DOCUMENTS

| | | |
|---|---|---|
| EP | 1736104 B1 | 3/2009 |
| EP | 2060234 A1 | 5/2009 |
| JP | 2005160933 A | 6/2005 |
| RU | 2080833 C1 | 6/1997 |
| WO | 8101953 A1 | 7/1981 |
| WO | 8501427 A1 | 4/1985 |
| WO | 8904146 A1 | 5/1989 |
| WO | 2008118728 A1 | 10/2008 |

OTHER PUBLICATIONS

Gong, S., "Perfectly Flexible Mechanism and Integrated Mechanism System Design", Mechanism and Machine Theory 39(2004), (Nov. 2004)—pp. 1155-1174.

International Search Report and Written Opinion for International Application No. PCT/US2014/048168, dated Apr. 9, 2015—8 pages.

(56) References Cited

OTHER PUBLICATIONS

Kolios et al., "Microlaparoscopy", J. Endourology 18(9), (Nov. 2004)—pp. 811-817.
Lim et al., "Application of Type Synthesis Theory to the Redesign of a Complex Surgical Instrument", Journal of Biomechanical Engineering (124), (Jun. 2004)—pp. 265-274.
Lim et al., "A Review of Mechanism Used in Laparoscopic Surgical Instruments", Mechanism and Machine Theory 38, (2003)—pp. 1133-1147.
Lim, J., "Type Synthesis of a Complex Surgical Device", Master Thesis, (Feb. 21, 2001)—45 pages.
Steichen et al., "Mechanical Sutures in Surgery", Brit. J. Surg. 60(3), (Mar. 1973)—pp. 191-197.

* cited by examiner

SURGICAL STAPLER AND FEEDER BELT CONFIGURATIONS

CROSS-REFERENCE TO RELATED APPLICATIONS

This patent application is a divisional application of U.S. application Ser. No. 14/339,054 filed on Jul. 23, 2014, now pending, which is a continuation application of U.S. patent application Ser. No. 13/746,449 filed on Jan. 22, 2013, now U.S. Pat. No. 9,386,986, which is a continuation application of U.S. patent application Ser. No. 13/282,759 filed on Oct. 27, 2011, now abandoned, which is a divisional application of U.S. patent application Ser. No. 14/477,834 filed on Jun. 3, 2009, now U.S. Pat. No. 8,056,789. U.S. patent application Ser. No. 13/746,449 is also a continuation application of U.S. patent application Ser. No. 13/090,168 filed on Apr. 19, 2011, now U.S. Pat. No. 8,365,973, which is a continuation application of U.S. patent application Ser. No. 12/477,834 filed on Jun. 3, 2009, now U.S. Pat. No. 8,056,789. The contents of the aforementioned related applications are incorporated herein by reference in their entireties.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter. That inconvenience may discourage surgeons from using the endocutter for procedures in which use of an endocutter may benefit the patient. Similar inconveniences may accompany the use of surgical staplers other than endocutters.

SUMMARY OF THE INVENTION

A surgical apparatus is configured to deploy a surgical staple, wherein the surgical staple is deformable from a first configuration (e.g., an un-deployed configuration) to a second deployed configuration in accordance with embodiments of the present invention. The surgical staple of this surgical apparatus includes a first leg and a second leg, wherein said surgical staple forms a substantially D-shape in said second deployed configuration.

The surgical apparatus is further configured to include a feeder belt to which at least one end of said first leg of the surgical staple may be frangibly affixed to said feeder belt, whereas one end of said second leg of the staple may be free (e.g., unattached or un-affixed to the feeder belt).

The surgical apparatus, in said second configuration, the ends of the staple as described may be closer to one another in the second configuration than in the first configuration.

The surgical apparatus, in said second configuration, the ends of the staple as described may contact one another.

The surgical apparatus, as deploying the surgical staple, the surgical staple may be plastically deformable from the first configuration to the second configuration.

The surgical apparatus, in the first configuration of the un-deployed surgical staple, the first leg of the surgical staple may be substantially straight and the second leg of the surgical staple may be at least partially curved.

The surgical apparatus, in the second deployed configuration, the surgical staple may form a completely closed D-shape.

The surgical apparatus, in the first configuration (e.g., un-deployed configuration), the surgical staple may be in a generally V-shaped form.

The surgical apparatus, in the first configuration (e.g., un-deployed configuration), the surgical staple may include a continuously curved segment.

A surgical apparatus for treating tissue in a surgical procedure comprises a surgical staple that includes a first leg and a second leg, wherein the surgical staple is configured to be deployed by deforming only the second leg. After deployment, the surgical staple substantially resembles a D-shape after the second leg is deformed.

A surgical apparatus for treating tissue in a surgical procedure comprises a surgical staple that includes a first leg and a second leg, wherein the surgical staple is configured to be deployed from a first configuration substantially resembling a V-shape to a second configuration substantially resembling a D-shape.

A surgical apparatus for treating tissue in a surgical procedure comprises a surgical staple that includes a first leg and a second leg, wherein the surgical staple is configured to be deployed by deforming the second leg only during deployment from a first configuration to a second configuration. The surgical staple is configured to substantially resemble a V-shape in the first configuration. The surgical staple is configured to substantially resemble a D-shape after deployment in the second configuration.

A surgical apparatus for treating tissue comprises a surgical staple that includes a first leg and a second leg, wherein deployment of said surgical staple by said surgical apparatus involves deforming only the second leg of said surgical staple. Deployment of said surgical staple by said surgical apparatus involves deforming said staple from a first configuration substantially resembling a V-shape or a suture needle to a second configuration substantially resembling a D-shape.

A surgical apparatus for treating tissues comprising a surgical staple that includes a first leg and a second leg, wherein deployment of said surgical staple by said surgical apparatus includes deforming said staple from a first configuration to a second configuration, wherein deforming said surgical staple involves only deforming said second leg of said surgical staple. In the first configuration, the first leg of the surgical staple is substantially straight and the second leg of the surgical staple is substantially curved. Furthermore, in the first configuration, the first leg and the second leg of the surgical staple forms s substantially V-shape configuration.

Alternatively or similarly, in the first configuration, the first leg and second leg of the surgical staple is in a configuration or shape substantially resembling a suture needle. In the second configuration, the first leg and the second leg of the surgical staple form a substantially D-shape configuration.

A surgical apparatus for treating tissues comprises a surgical staple that includes a first leg and a second leg, wherein deployment of said surgical staple by said surgical apparatus includes deforming said surgical staple from a first configuration to a second configuration, wherein deforming said surgical staple involves only deforming said second leg of said surgical staple to form a substantially D-shape in said second configuration. In the first configuration, the first leg and the second leg of the surgical staple form a substantially V-shape. In the first configuration, the first leg of the surgical staple is substantially straight and the second leg of the surgical staple is substantially curved. In the second configuration, the first leg of the surgical staple remains substantially straight and the second leg of the surgical staple remains substantially curved.

A method of treat tissue using an exemplary surgical apparatus, which involves urging a surgical staple into tissue, while the surgical staple is in a first shape, and deforming the surgical staple from the first shape into a second shape that is substantially a D-shaped.

BRIEF DESCRIPTION OF THE DRAWINGS

The use of the same reference symbols in different figures indicates similar or identical items.

DETAILED DESCRIPTION

Figure 1:
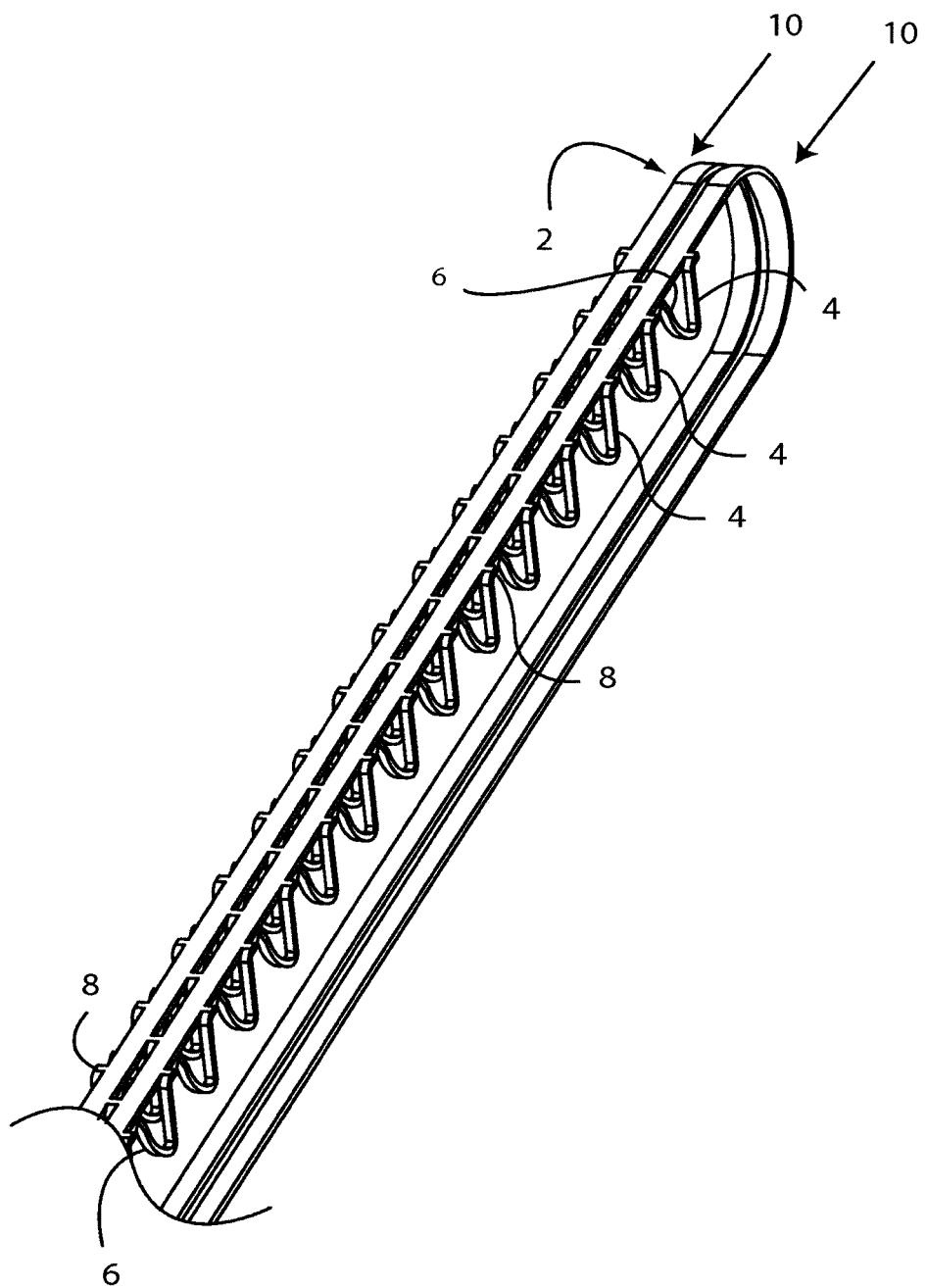
FIG. 1 is a perspective view of an exemplary feeder belt with staples affixed thereto.

U.S. patent application Ser. No. 12/263,171, filed on Oct. 31, 2008 (the "Endocutter Document"), is hereby incorporated by reference herein in its entirety. The Endocutter Document describes exemplary feeder belts used in a surgical stapler. Referring to FIG. 1, a feeder belt 2 may be a long, narrow, thin strip of material from which one or more staples 4 extend. The feeder belt 2 and staples 4 of the present document may be substantially as set forth in the Endocutter Document, with the exception of the inventive features set forth in the present document. Each staple 4 may have a free end 6, and an opposite end 8 that is connected to the feeder belt 2. Advantageously, the staples 4 are frangibly affixed to the feeder belt 2, such that they are sheared off from the feeder belt 2 during deployment. However, the staples 4 may be connected to the feeder belt 2 in any suitable manner. One or more rows 10 of staples 4 may be connected to the feeder belt 2. Each row 10 of staples 4 is the group of staples 4 positioned at substantially the same lateral location relative to the longitudinal centerline of the feeder belt 2, and each row 10 of staples 4 may be oriented generally longitudinally. After deployment, each staple 4 may form substantially a D-shape. As seen in FIG. 1, an exemplary feeder belt 2 may be a generally flat and generally linear piece of material that carries a plurality of staples 4. The feeder belt 2 may lie substantially in a single plane. The feeder belt 2 may be flexible, or instead may be rigid.

Figure 2:
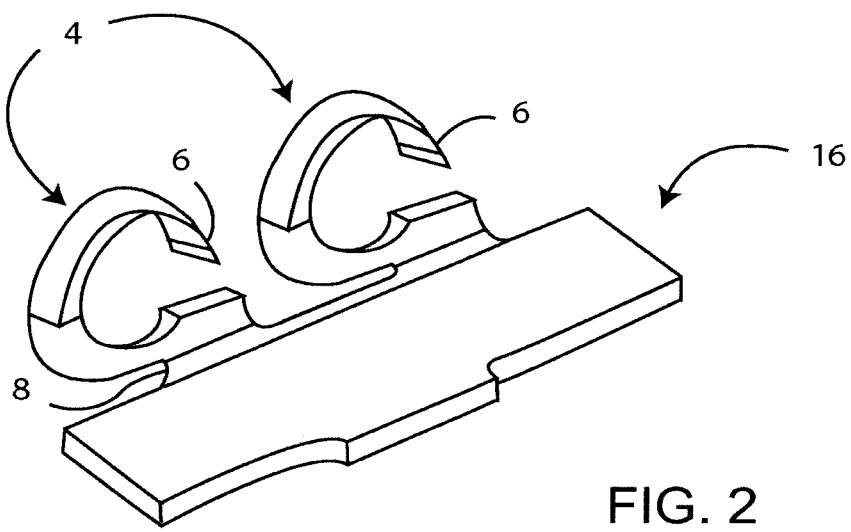
FIG. 2 is a perspective view of a carrier with staples affixed thereto.
Figure 3:
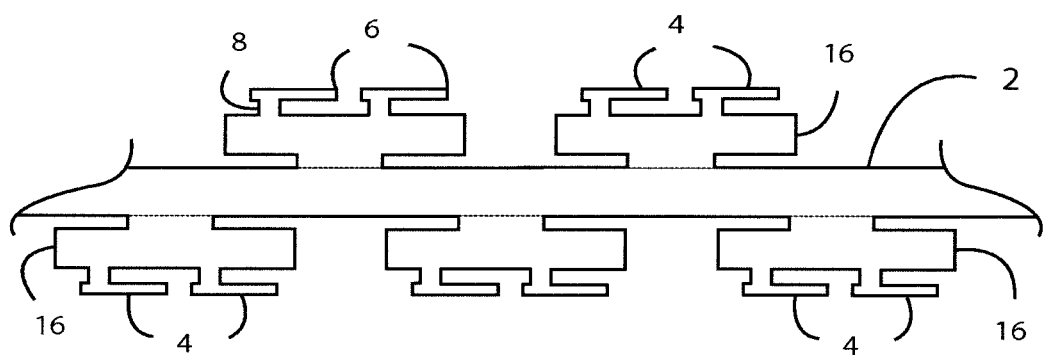
FIG. 3 is a top view of carriers and staples of FIG. 2 attached to an exemplary feeder belt.

Referring also to FIGS. 2-3, at least two staples 4 may be generally D-shaped, and may extend from a carrier 16. This configuration of staples 4 may be referred to as the "double-D configuration." The end 8 of each staple 4 that is connected to the carrier 16 may be fixed to that carrier 16 such that the staples 4 are not frangibly separable from the carrier 16. Instead, the carrier 16 may itself be fixed to and frangibly separable from the feeder belt 2. In this way, the carrier 16 is implanted in tissue along with the attached staples 4. The connection between the carrier 16 and the feeder belt 2 may be coined or otherwise fabricated to facilitate frangible separation from the feeder belt 2. Such a connection may be made in the same or similar manner as between a staple 4 and the feeder belt 2 as set forth in the Endocutter Document, or in a different manner. As shown in FIG. 2, staples 4 that are attached to a carrier 16 may be substantially in the same plane as one another, such that the staples 4 all extend from the same side of the carrier 16. Further, those staples 4 may be oriented in substantially the same direction as one another, such that the free end 6 of each staple 4 is located at the proximal end or at the distal end of each staple 4. Alternately, at least one staple 4 attached to a carrier 16 may be oriented in a different direction relative to a least one other staple 4. At least one carrier 16 may be in substantially the same plane as the feeder belt 2, and positioned lateral to the feeder belt 2.

Figure 4:
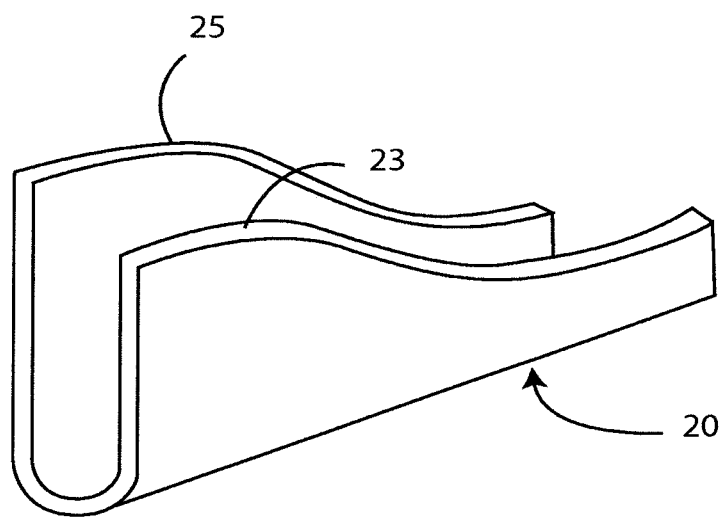
FIG. 4 is a perspective view of an exemplary wedge.

Referring also to FIG. 4, the wedge 20 used to form the staples 4 and then shear the carrier 16 from the feeder belt 2 may have a three-dimensional form. That is, the wedge 20 may include two separate ramps 22, 24, where the first ramp 22 is configured to deform staples 4 and the second ramp 24 is configured to shear the carriers 16 from the feeder belt 2. The wedge 20 may be actuated substantially as described in the Endocutter Document, with the following differences. The first ramp 22 may be located laterally outboard relative to the second ramp 24. As the wedge 20 slides relative to the feeder belt 2, the first ramp 22 sequentially engages staples 4, deforming them upward into contact with an anvil which causes further deformation. The first ramp 22 is shaped to facilitate that deformation, such as set forth in the Endocutter Document. The second ramp 24 may be located laterally inboard relative to the first ramp 22. The second ramp 24 is shaped such that, after the staples 4 attached to a carrier 16 have been deformed by contact with the first ramp 22, the second ramp 24 contacts and exerts a force on the carrier 16 and/or the junction between the feeder belt 2 and that carrier 16 in order to shear off or otherwise separate the carrier 16 from the feeder belt 2. Alternately, instead of a three-dimensional wedge 20 with two separate ramps 22, 24, two separate wedges 20 may be utilized, where one wedge 20 deforms staples 4 and the other wedge 20 shears carriers 16 from the feeder belt 2.

Figure 5:
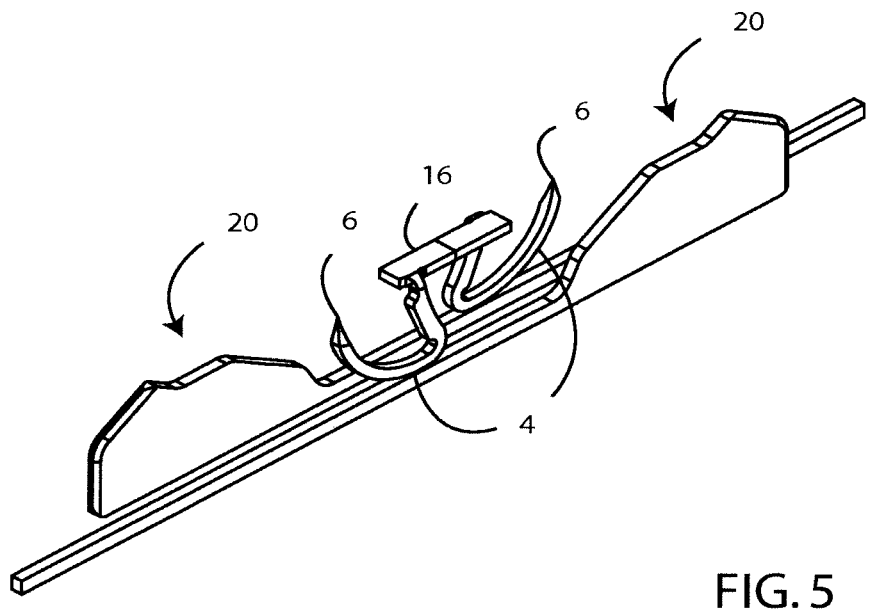
FIG. 5 is a perspective view of another exemplary carrier with staples affixed thereto, prior to deployment.
Figure 6:
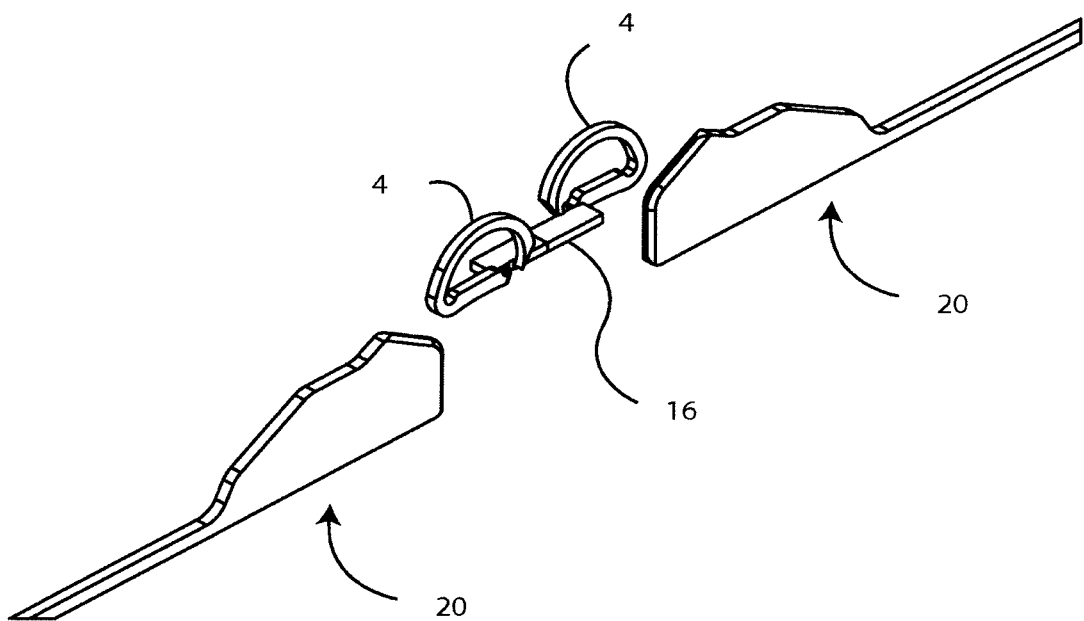
FIG. 6 is the perspective view of FIG. 5, after deployment.

Alternately, at least one staple 4 that is attached to a carrier 16 may be out of plane relative to at least one other staple 4 that is attached to that carrier 16. Referring also to FIG. 5, a carrier 16 may have two or more staples 4 extending therefrom, where at least one staple 4 extends from a different side of the carrier 16 than at least one other staple 4. At least one staple 4 may be oriented in a different direction from at least one other staple 4. For example, as shown in FIG. 5, two staples 4 may be attached to a carrier 16, where the free end 6 of one staple 4 is located at the proximal end of that staple 4, and the free end 6 of the other staple 4 is located at the distal end of that staple 4. This configuration of the staples 4 may be referred to as the "B configuration." Two separate wedges 20 may be utilized in conjunction with the staples 4 and carrier 16. Those two wedges 20 may move in opposite directions relative to one another, referring also to FIG. 6, to deform the staples 4. One of the wedges 20 may be configured substantially as shown in FIG. 4 such that the wedge 20 can both deform one or more staples 4 and shear the carrier 16 from the feeder belt 2. The resultant combination of the deformed staples 4 and carrier 16 may form generally a B-shape. Alternately, both wedges 20 may be configured as set forth in the Endocutter Document, and the staples 4 may be connected to the feeder belt 2 directly instead of to a carrier 16.

Figure 7:
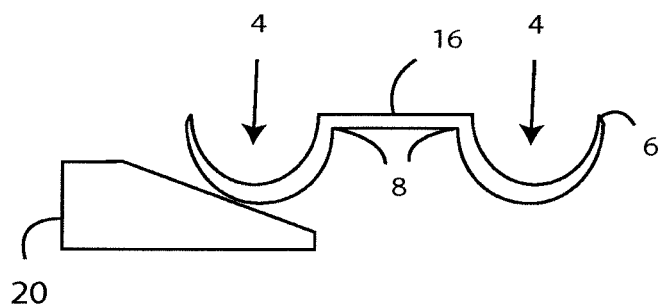
FIG. 7 is a side view of an exemplary staple in a first state.
Figure 8:
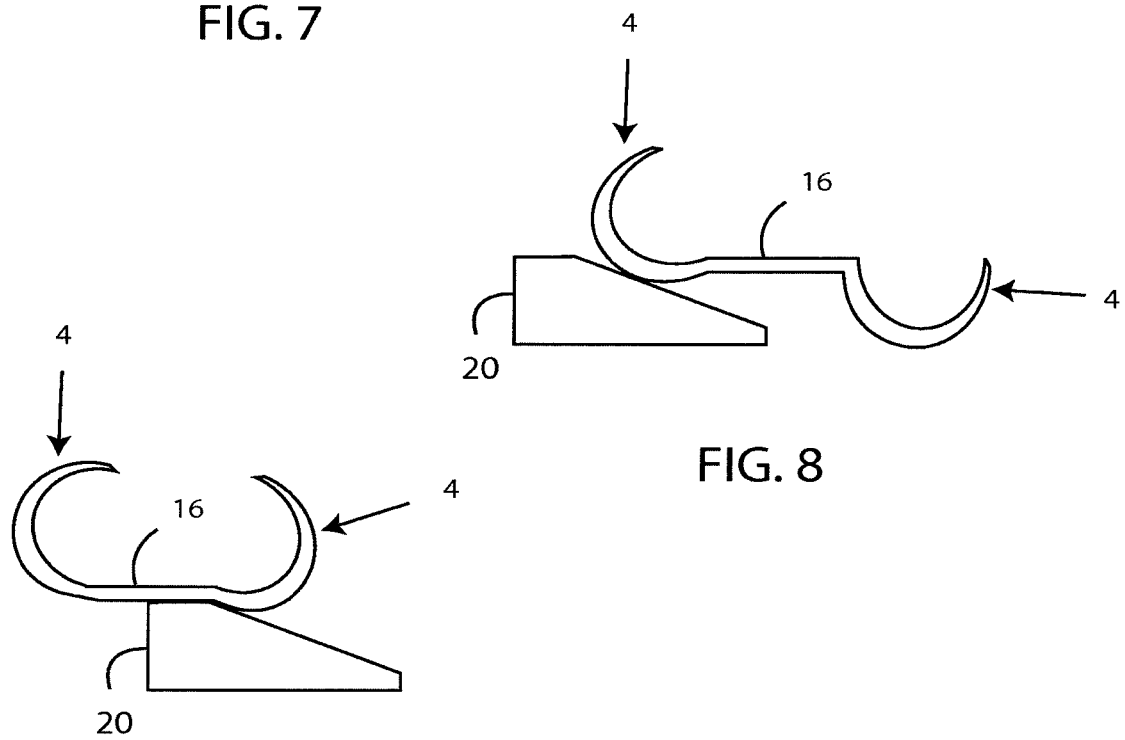
FIG. 8 is a side view of the exemplary staple of FIG. 7 in a second state.
Figure 9:
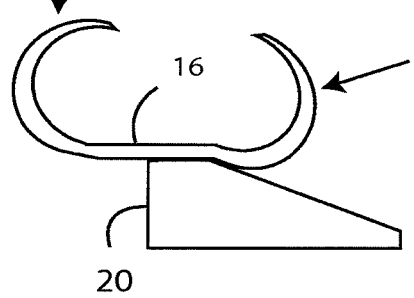
FIG. 9 is a side view of the exemplary staple of FIG. 7 in a third state.
Figure 10:
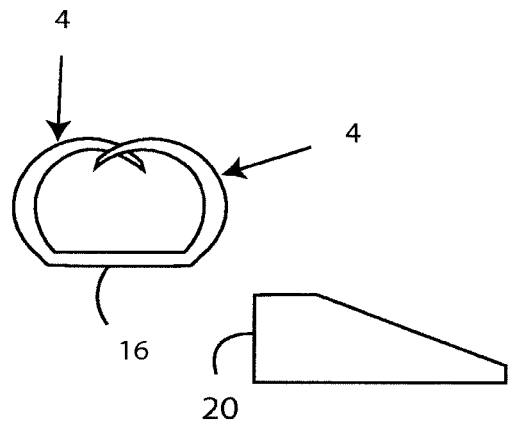
FIG. 10 is a side view of the exemplary staple of FIG. 7 in a fourth, deployed state.

Referring also to FIGS. 7-10, staples 4 may be formed into a B-configuration with a wedge 20 moving in a single direction. Such staples 4 may be attached to a carrier 16 substantially coplanar with one another, similar to the configuration of FIG. 2. As another example, at least two staples 4 may be attached to a carrier 16 out of plane relative to one another, similar to the configuration of FIG. 5. As seen in FIG. 7, at least one staple 4 may be oriented relative to a wedge 20 such that the free end 6 is longitudinally closer to the wedge 20 as it approaches the staple 4 than the opposite end 8. The surface of the wedge 20 that contacts that staple 4, and the staple 4 itself, are shaped such that contact therebetween as the wedge 20 slides relative to the staple 4 urges the free end 6 of the staple 4 upward, referring also to FIG. 8. As the wedge 20 continues to slide relative to the staples 4, the wedge 20 encounters the next longitudinally-successive staple 4, and urges that staple 4 upward as well, referring also to FIG. 9. Optionally, two wedges 20 may be used where at least two staples 4 attached to a carrier 16 are out of plane relative to each other. After the wedge 20 has deformed both staples 4, the staples 4 are in the B-configuration, as shown in FIG. 10. The carrier 16 may then be separated from the feeder belt 2 by the wedge 20. Optionally, the three-dimensional wedge 20 of FIG. 4 may be utilized in order to first form the staples 4 and then separate the carrier 16 from the feeder belt 2.

Figure 11:
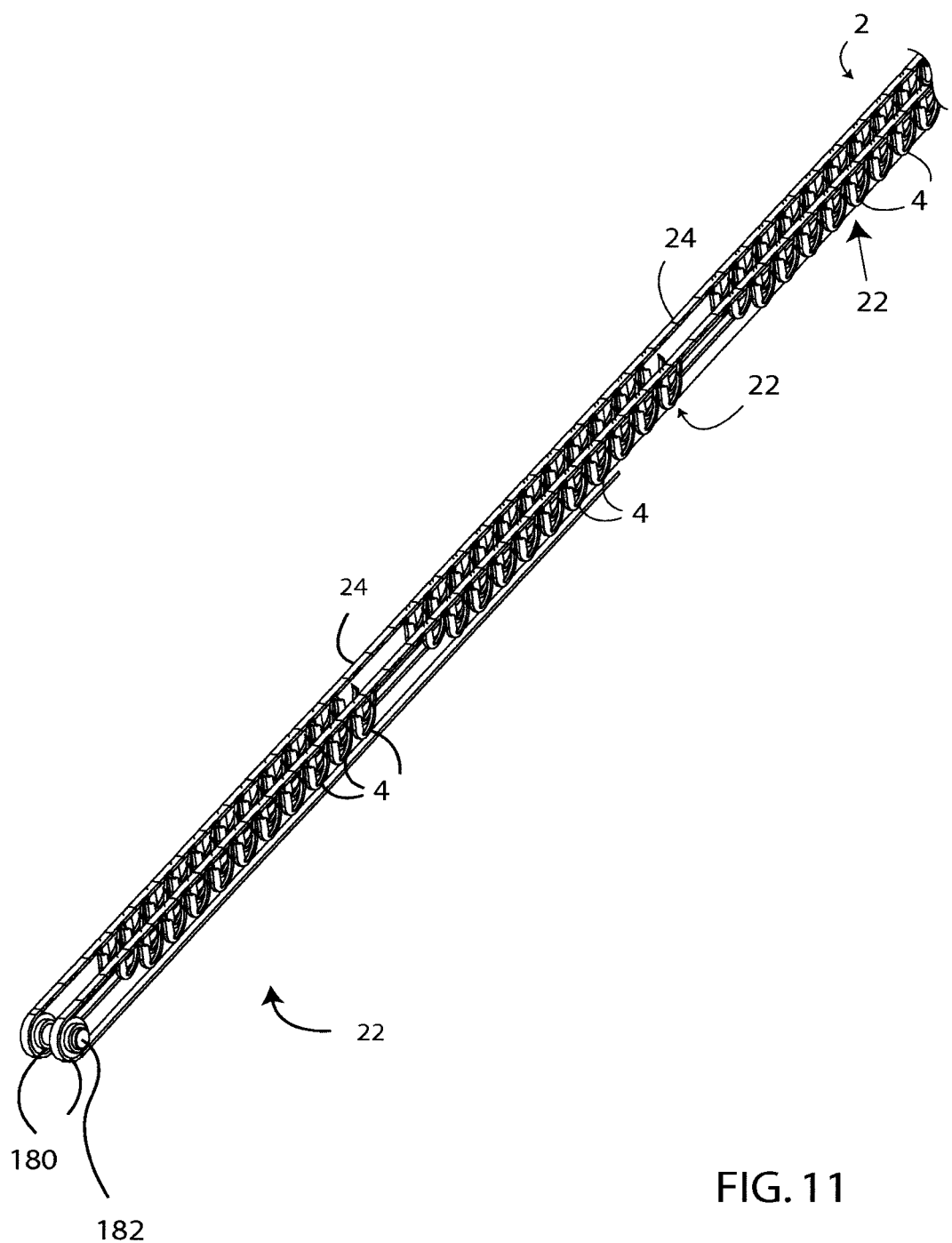
FIG. 11 is a perspective view of an exemplary feeder belt with groups of staples affixed thereto.
Figure 12:
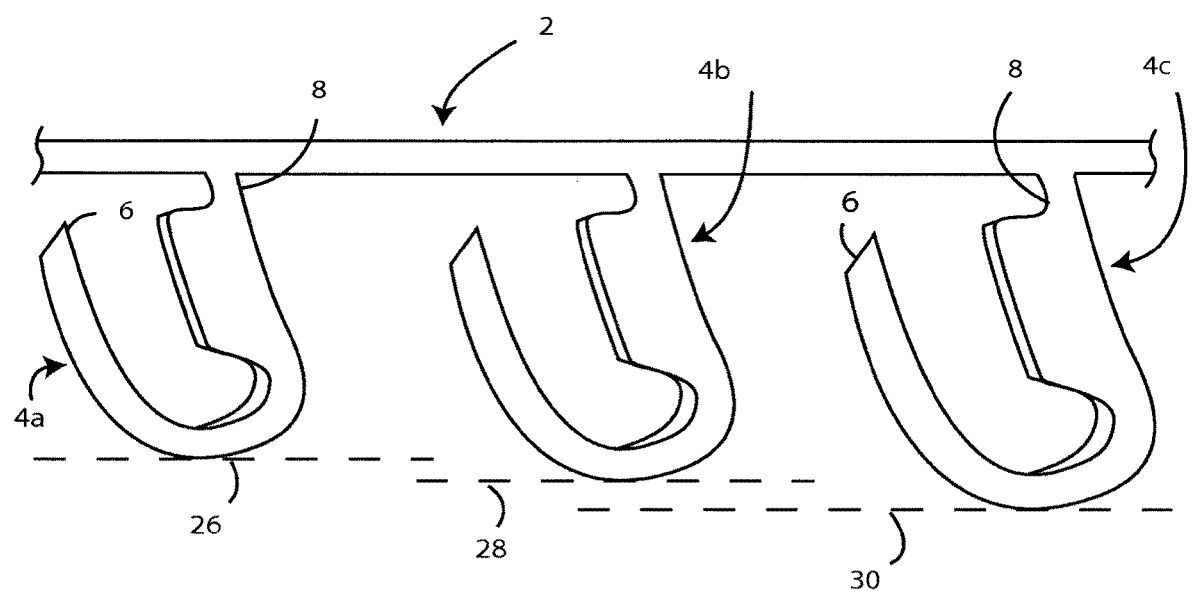
FIG. 12 is a side view of an exemplary feeder belt from which differently-sized staples extend.

The staples 4 may be grouped together along the feeder belt 2 in any suitable manner. As one example, referring also to FIG. 11, the staples 4 may be organized into two or more groups 22 longitudinally spaced apart from one another by blank space 24 along the feeder belt 2. The blank space 24 may have any suitable length. Advantageously, no staples 4 extend from the feeder belt 2 along a blank space 24 on the feeder belt 2. At least one staple 4 may be deployable to a different closed shape than at least one other staple 4. As one example, referring also to FIG. 12, the staples 4 within a group 22 need not be homogeneous. For example, one or more staples 4 may extend downward from the feeder belt 2 a distance greater than one or more other staples 4. A staple 4a may extend downward from the feeder belt 2 a first distance 26. Another staple 4b may extend downward from the feeder belt 2 a second distance 28 greater than the first distance 26. Yet another staple 4c may extend downward from the feeder belt 2 a third distance 30 greater than the second distance 28 The staple 4c may be larger than the staples 4a, 4b. The staples 4a, 4b, 4c may be positioned longitudinally relative to one another in any suitable manner. Advantageously, non-homogeneous staples 4 are positioned longitudinally relative to one another, and differ from one another, in a manner related to a specific surgical procedure to be performed. For example, staple 4a is positioned proximal to staple 4b, which in turn is positioned proximal to staple 4c. In this way, tissue that varies in thickness in a known way may be stapled effectively, where the tissue becomes thicker from the proximal to the distal direction. A staple 4 that extends further downward from the feeder belt 2 may rotate about its attached end 8 substantially the same amount rotationally as a staple 4 extends a lesser distance downward from the feeder belt 2. As a result, the free end of 6 a staple 4c that extends a third distance 30 downward from the feeder belt 2 will swipe through tissue at a height above the feeder belt 2 that is above the height through which the free end of a staple 4a extends a first distance 26 downward from the feeder belt 2 can swipe, where the first distance 26 is less than the third distance 30. As another example, one or more staples 4 may be shaped differently from one or more other staples 4, whether or not a subset of those staples 4 extends downward a different distance from the feeder belt 2 than a different subset of those staples 4. As another example, one or more staples 4 within a group 22 may have a D-configuration after formation and shearing, and one or more staples 4 within the same group 22 may have a B-configuration, a double-D configuration, and/or any other suitable configuration. One or more staples 4 within a group 22 may vary from one or more other staples 4 within the same group 22 in any other suitable matter. Alternately, all of the staples 4 within at least one group 22 may be substantially homogeneous.

Figure 13:
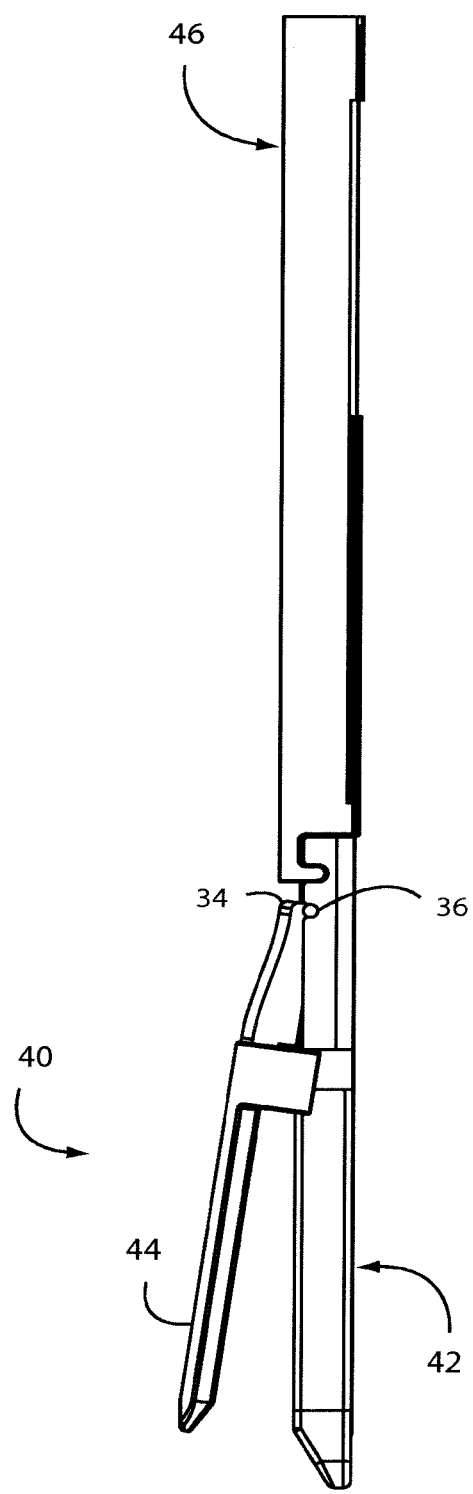
FIG. 13 is a side view of an exemplary surgical instrument with an anvil and staple holder.
Figure 14:
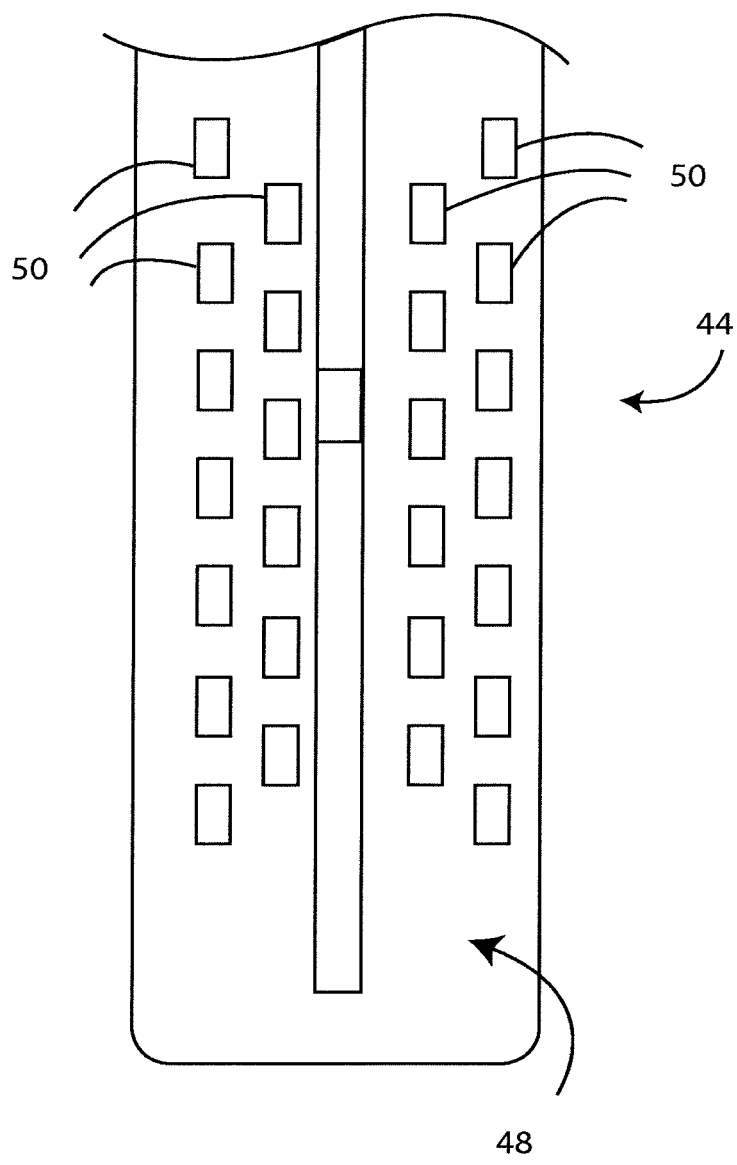
FIG. 14 is a bottom view of an exemplary anvil.

Referring also to FIGS. 13-14, as set forth in the Endocutter Document, a surgical instrument that deploys staples 4 from the feeder belt 2 may include an end effector 40 that includes a staple holder 42 and an anvil 44. One or more feeder belts 2 may extend through a shaft 46 proximal to and connected to the end effector 40, into the staple holder 42. An inner surface 48 of the anvil 44, which is the surface of the anvil 44 oriented generally toward the staple holder 42, may include staple forming pockets 50 defined therein. As the staples 4 are deployed, the free end 6 of each staple 4 may be forced into a corresponding staple forming pocket 50, whereby contact between the free end 6 of that staple 4 and the staple forming pocket 50 causes that staple 4 to close. Each staple forming pocket 50 may be shaped in any suitable manner.

Figure 15:
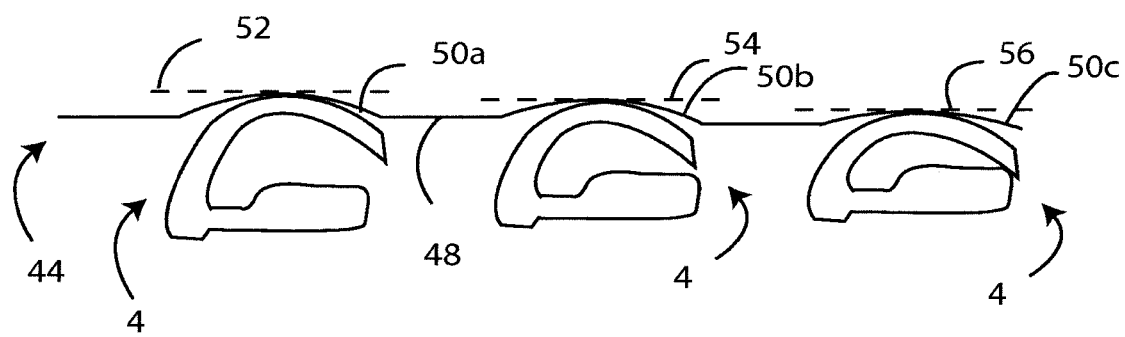
FIG. 15 is a side cross-section view of an anvil with non-homogeneous staple pockets defined therein.

Referring also to FIG. 15, the staple forming pockets 50 need not be homogeneous. As one example, one or more staple forming pockets 50 may extend further into the inner surface 48 of the anvil 44 then one or more other staple forming pockets 50. One anvil forming pocket 50a may extend a first distance 52 above the inner surface 48 of the anvil 44. Another anvil forming pocket 50b may extend a second distance 54 above the inner surface 48 of the anvil 44, where the second distance 54 may be less than the first distance 52. Another anvil forming pocket 50c may extend a third distance 56 above the inner surface 48 of the anvil 44, where the third distance 56 may be less than the second distance 54. As another example, at least one staple forming pocket 50 may be curved or shaped in a different manner than at least one other staple forming pocket 50. For example, one staple forming pocket 50 may have a tighter radius of curvature than a different staple forming pocket 50. As another example, one staple forming pocket 50 may have a complex shape, and another staple forming pocket 50 may simply be arcuate. In this way, different anvil forming pockets 50a, 50b, 50c may form corresponding staples 4 differently. Non-homogeneous anvil forming pockets 50 may be utilized with a feeder belt 2 that utilizes at least one group 22 of staples 4 that is homogeneous, such that different degrees of bending and forming may be applied across a variety of staples 4 that are substantially the same in order to obtain the result of closed staples 4 that are differentially formed. As another example, non-homogeneous anvil forming pockets 50 may be utilized with non homogeneous staples 4, such as those described above, where particular staples 4 are positioned for deployment into particular, corresponding anvil forming pockets 50.

As another example, the inner surface 48 of the anvil 44 need not be flat, such that different anvil forming pockets 50 may be located at a different distance away from the staple holder 42 when the end effector 40 is closed. In this way, staples 4 of different heights may be accommodated. As another example, the gap between the inner surface 48 of the anvil 44 and the staple holder 42 may be adjustable, whether the inner surface 48 is substantially flat or not. In this way, the degree of deformation of the staples 4 within a particular tissue structure held between the anvil 44 and the staple holder 42 may be controlled. The gap may be adjustable in any suitable manner, such as by mechanisms, structures, or methods set forth in co-pending U.S. patent application Ser. No. 12/477,302, filed on Jun. 3, 2009, which is hereby incorporated by reference in its entirety.

Figure 16:
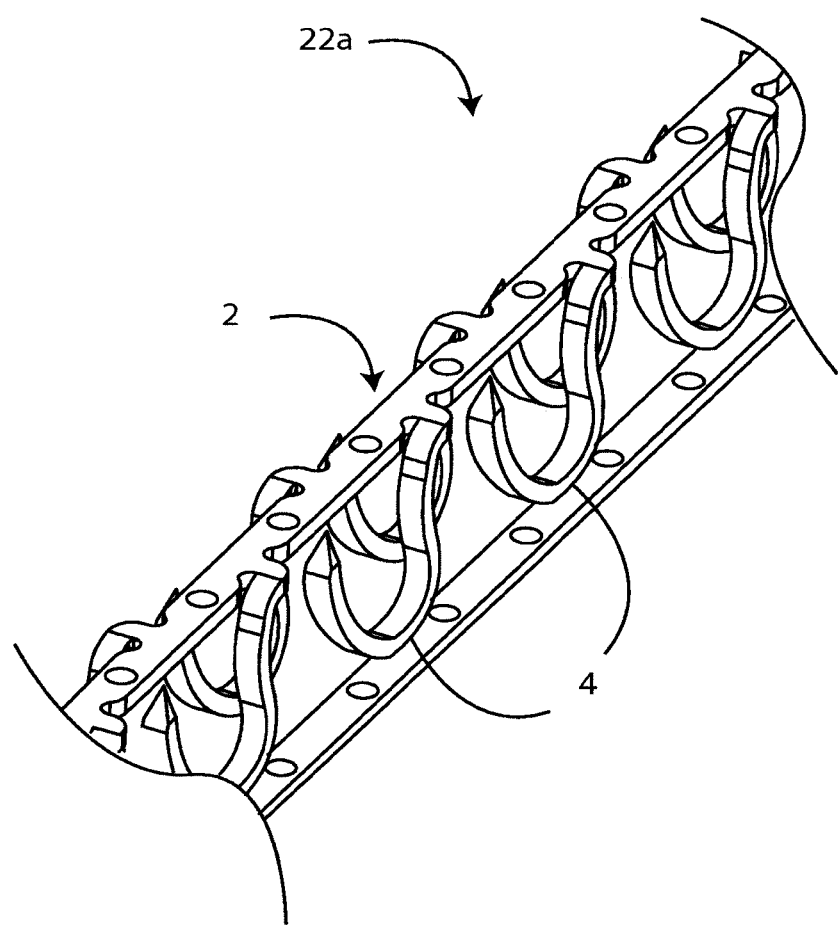
FIG. 16 is a perspective view of a first group of staples extending from a corresponding feeder belt.
Figure 17:
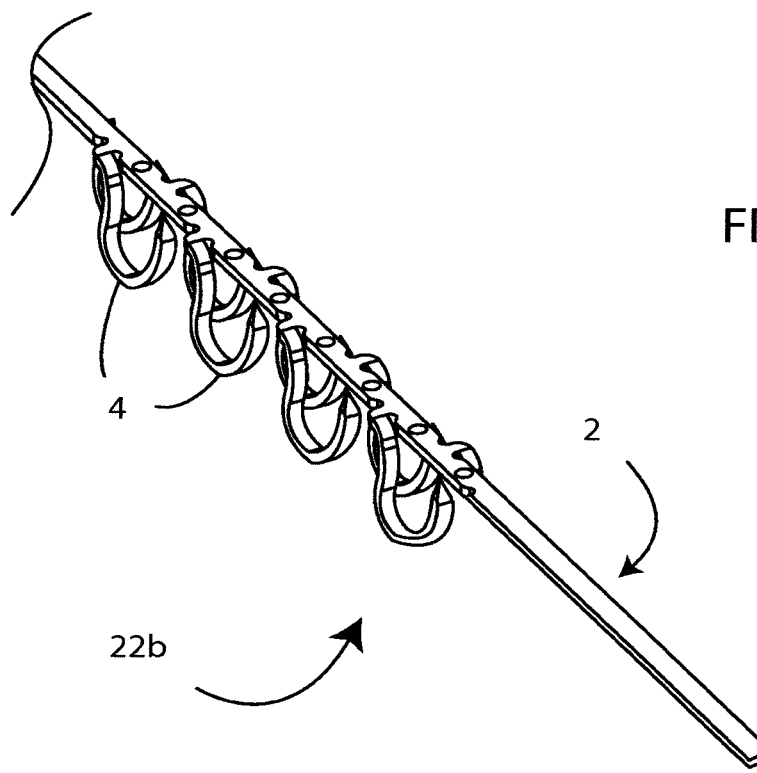
FIG. 17 is a perspective view of a second group of staples extending from the feeder belt of FIG. 16.
Figure 18:
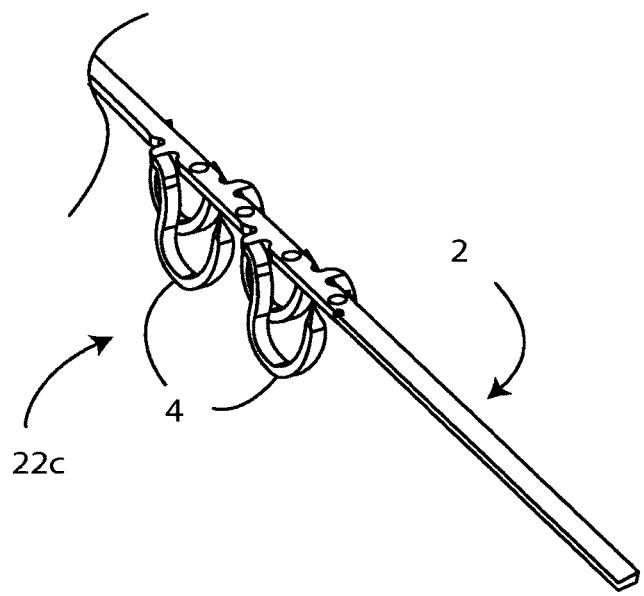
FIG. 18 is a perspective view of a third group of staples extending from the feeder belt of FIG. 16.
Figure 19:
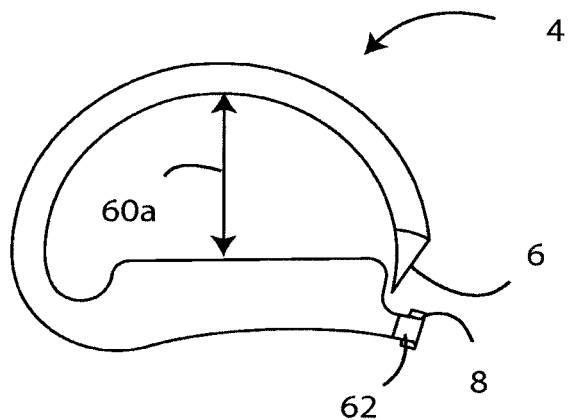
FIG. 19 is a side view of an exemplary variable-thickness staple in a first configuration.
Figure 20:
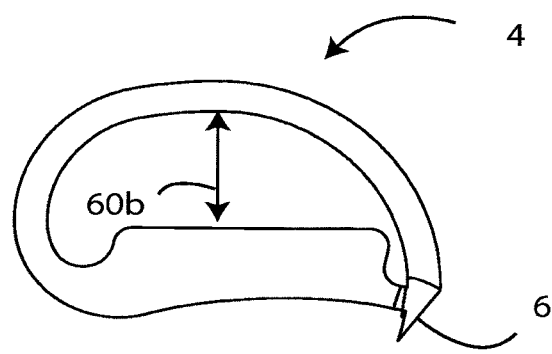
FIG. 20 is a side view of the staple of FIG. 19 in a second configuration.
Figure 21:
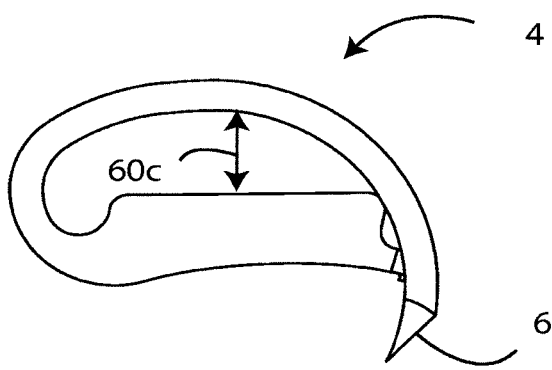
FIG. 21 is a side view of the staple of FIG. 19 in a third configuration.

Referring also to FIGS. 16-18, staples 4 on a feeder belt 2 may form longitudinally-successive groups 22 in which at least one group 22 may have a different number or configuration of staples 4 than at least one other group 22. Such an organization of staples 4 may be advantageous for particular surgical procedures. Referring to FIG. 16, a first group 22a of staples 4 may be connected to a feeder belt 2. Referring to FIG. 17, a second group 22b of staples 4 may be connected to the feeder belt 2 proximal to the first group 22a. The first group 22a of staples 4 may include a different number of staples 4 than the second group 22b. Referring to FIG. 18, a third group 22c of staples 4 may be connected to the feeder belt 2 proximal to the second group 22b. The third group 22c of staples 4 may include a different number of staples 4 than the first group 22a and/or the second group 22b. The first group 22a is deployed before the second group 22b, which in turn is deployed before the third group 22c. Where each group 22a, 22b, 22c includes successively fewer staples 4 than the previous one, that configuration of feeder belt 2 may be suitable for a surgical procedure in which tissue structures of increasingly narrow widths are treated with the feeder belt 2.

Where a variable gap between the anvil 44 and staple holder 42 in the closed position of the end effector 40 is provided, the staples 4 may be configured in any manner to take advantage of that variable gap. As one example, referring also to FIGS. 19-21, at least one staple 4 may be configured to be closed through a variety of degrees. Referring to FIG. 19, a staple 4 may be closed to a first degree in which both sides of the staple 4 are closed to a first distance 60a. That first distance 60a may result from a first gap between the anvil 44 and the staple holder 42. Referring also to FIG. 20, a staple 4 may be closed to a second degree in which both sides of the staple 4 are closed to a second distance 60b, which may be less than the first distance 60a, and which may result from a second gap between the anvil 44 and the staple holder 42 that is less than the first gap. Referring also to FIG. 21, a staple 4 may be closed to a third degree in which both sides of the staple 4 are closed to a third distance 60c, which may be less than the first distance 60a and the second distance 60b, and which may result from a third gap between the anvil 44 and the staple holder 42 that is less than the first gap and the second gap.

The staple 4 may be configured in any manner to close through a variety of tightnesses 60a, 60b, 60c without causing interference between the free end 6 of the staple 4 and a remainder of the staple 4. As one example, at least one staple 4 may include a notch 62 at or near the end 8 of the staple 4 that is fixed to the feeder belt 2. Such a notch 62 reduces the thickness of the staple 4, such that the free end 6 of the staple 4 can travel within that notch as the staple 4 is closed to a degree in which the free end 6 would otherwise collide and interfere with the staple 4 in the vicinity of the end 8. As another example, at least one staple 4 may be curved laterally such that contact between the free end 6 and a staple-forming pocket causes the free end 6 of the staple 4 to move laterally to and swipe past the other end 8 of the staple 8 as a consequence of the shape of the staple 4. As another example, the shape of at least one staple forming pocket 50 actively deflects the free end 6 of at least one staple 4 laterally, allowing it to swipe past the opposite end 8 of the staple 4 as a consequence of the shape of the staple forming pocket 50. Such a staple-forming pocket 50 alternately may be used in conjunction with a laterally-curved staple 4 such as described immediately above. As another example, the free end 6 of the staple 4 and/or a remainder of the staple 4 may be shaped such that contact between the free end 6 and a remainder of the staple 4 causes the free end 6 to deflect laterally and prevent interference therebetween. To that end, the free end 6 may be conical or otherwise curved, as may a remainder of the staple 4.

Figures 22, 23:
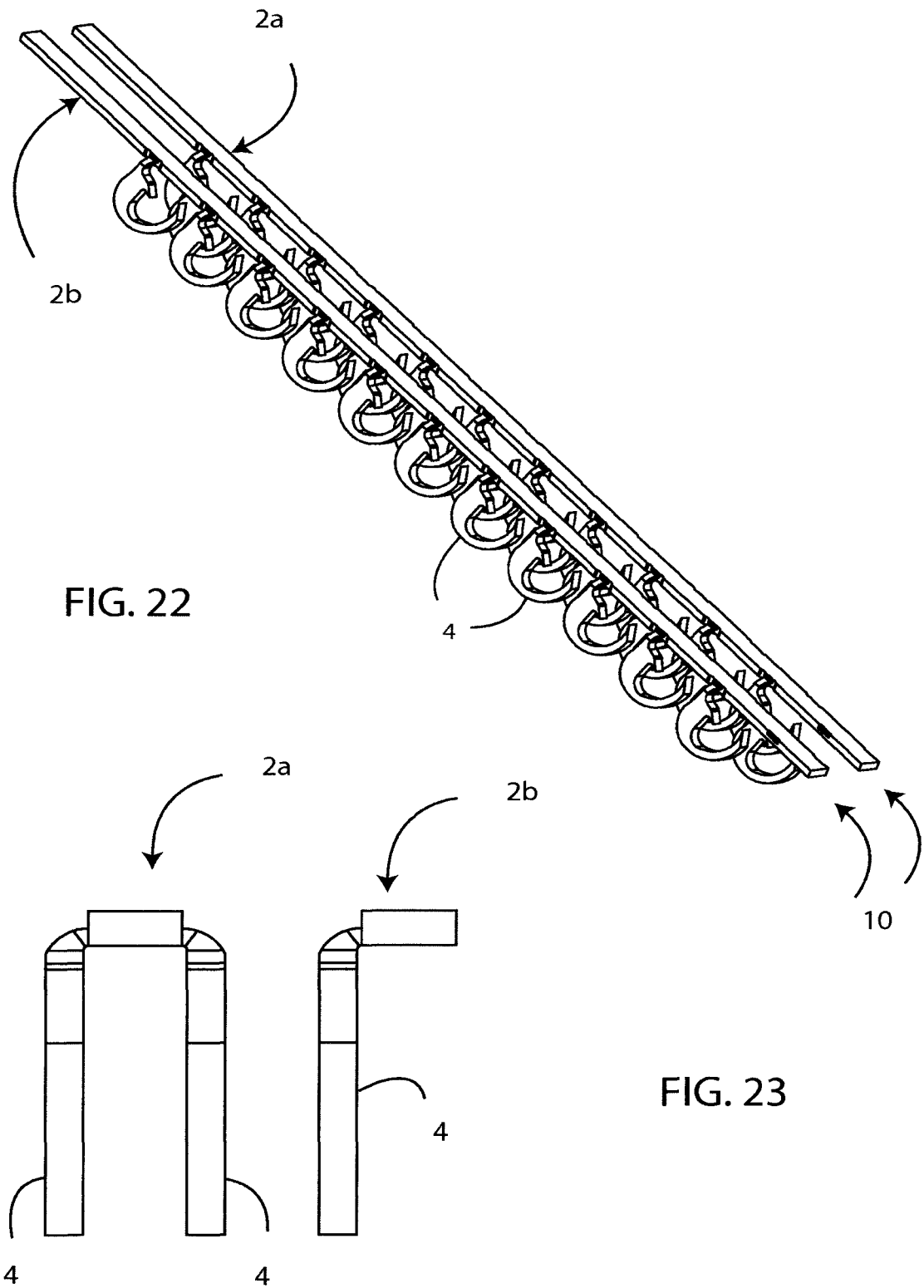
FIG. 22 is a perspective view of two exemplary feeder belts configured to deliver collectively three rows of staples.
FIG. 23 is an end view of the feeder belts of FIG. 22.

Multiple feeder belts 2 may be utilized in the staple holder 42 in order to provide any suitable number of rows 10 of staples 4 on each side of a knife held by the staple holder 42 that is used for transection or other incision in tissue made by the end effector 40. Referring also to FIGS. 22-23, two feeder belts 2 may be utilized on one or both sides of a transection, where one feeder belt 2a includes two rows 10 of staples 4 such as described above with regard to FIG. 1. The other feeder belt 2b may include a single row 10 of staples 4 configured in any suitable manner. As one example, for ease of fabrication, the feeder belt 2a may be configured in substantially the same way as the feeder belt 2b, where fabrication of a second row 10 of staples 4 is simply omitted from the feeder belt 2b. Alternately, the feeder belt 2b may have any other configuration of staples 4. For example, the staples 4 extending from feeder belt 2b need not be positioned in a row 10, and instead may be laterally staggered relative to one another. Alternately, two feeder belts 2 each may include two rows 10 of staples 4, such that four rows 10 of staples 4 may be deployed on each side of the transection. In this way, fabrication of the feeder belts 2 may be simplified, because the same feeder belt 2 may be utilized multiple times without the need to fabricate a different configuration of feeder belt 2.

Figure 24:
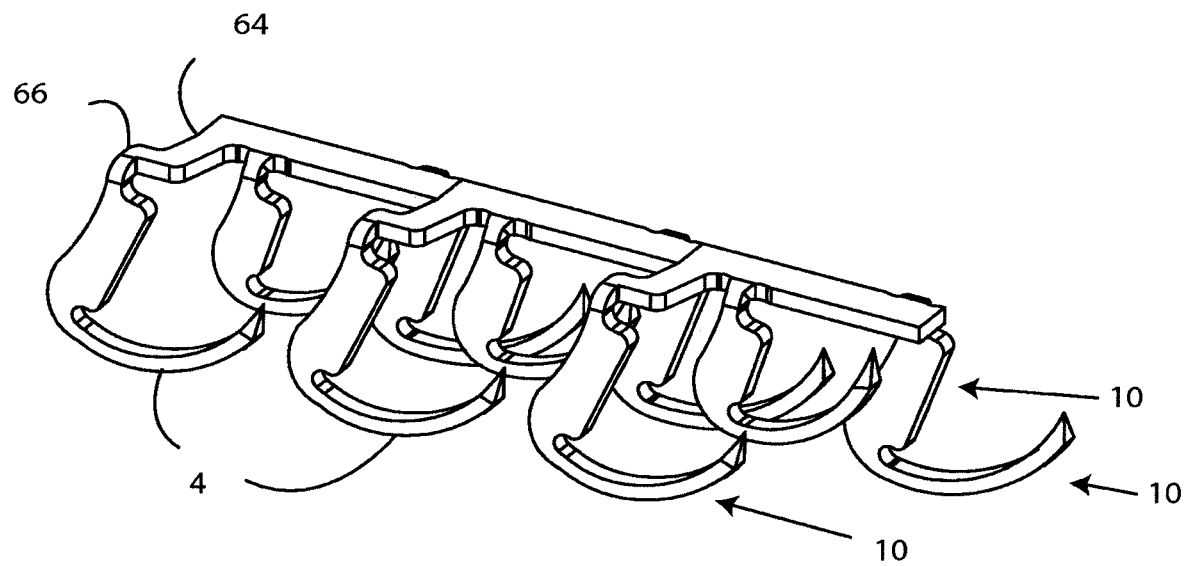
FIG. 24 is a perspective view of an exemplary feeder belt from which three rows of staples extend.

Alternately, three or more rows 10 of staples 4 may be attached to a single feeder belt 2. Referring also to FIG. 24, two rows 10 of staples 4 may be attached to the feeder belt 2 substantially as described in the Endocutter Document. A third row 10 may be provided by attaching staples 4 to the feeder belt 2 individually with extension arms 64. At least one extension arm 64 may extend generally laterally to the feeder belt 2, in a direction that may be substantially perpendicular to the longitudinal centerline of that feeder belt. At least one extension arm 64 may be substantially in the same plane as the corresponding feeder belt 2. Alternately, at least one extension arm 64 may be oriented or configured differently relative to the feeder belt 2. The staple 4 may be configured to be sheared off or otherwise separated from a lateral end 66 of the extension arm 64, such as by the three-dimensional wedge 20 of FIG. 4. Alternately, at least one extension arm 64 may be sheared off from or otherwise separated from the feeder belt 2, and may remain fixed to the staple 2. Advantageously, each extension arm 64 is connected to one corresponding staple 4. Alternately, at least one extension arm 64 may have two or more staples 4 connected thereto and extending therefrom. A staple 4 fixed to a corresponding extension arm 64 may be spaced laterally apart from the feeder belt 2.

Figure 25:
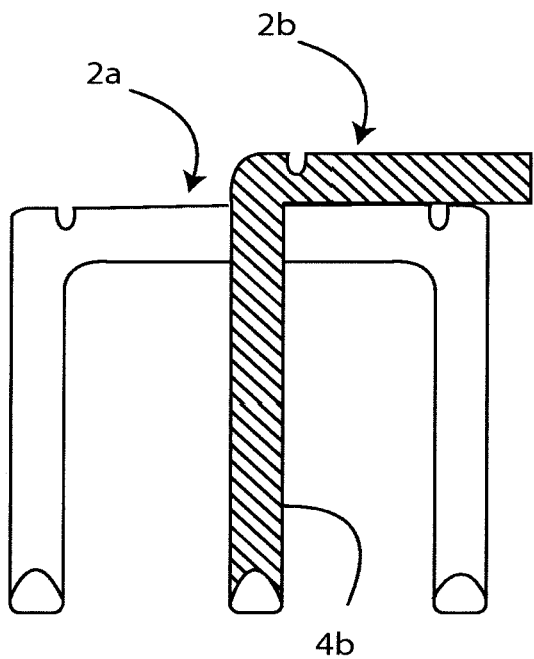
FIG. 25 is an end of an exemplary feeder belt assembly from which three rows of staples extend.
Figure 26:
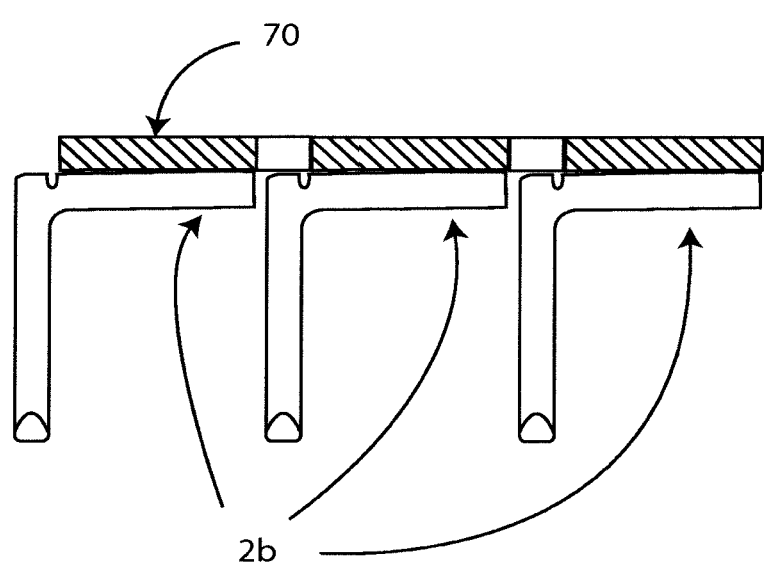
FIG. 26 is an end of another exemplary feeder belt assembly from which three rows of staples extend.

Alternately, a feeder belt 2 having three or more rows 10 of staples 4 attached to a single feeder belt 2 may be fabricated differently. As one example, referring to FIG. 25, a feeder belt 2a may be provided, along with a feeder belt 2b, such as described above with regard to FIG. 23. The feeder belt 2b may be generally L-shaped as viewed from the end. The feeder belt 2a may include a plurality of apertures therethrough. The feeder belt 2b may be fastened to an upper surface of the feeder belt 2a, such that the staples 4b of the feeder belt 2b extend through the apertures in the feeder belt 2a and beneath the feeder belt 2a. The feeder belt 2b may be fastened to the upper surface of the feeder belt 2a by laser welding or in any other suitable manner. Alternately, referring to FIG. 26, a master belt 70 may be provided, where one or more L-shaped feeder belts 2b are attached to the underside thereof by laser welding or in any other suitable manner. The master belt 70 need not have staples 4 extending therefrom, and may simply carry one or more L-shaped feeder belts 2b. Alternately, the master belt 70 may be fastened to one or more two-row feeder belts 2a. Alternately, the master belt 70 may include a plurality of apertures therethrough. At least one feeder belt 2b may be fastened to an upper surface of the master belt 70, such that the staples 4b of the feeder belt 2b extend through the apertures in the master belt 70 and beneath the feeder belt 70.

The feeder belts 2 described herein may be actuated such as described in this document, in the Endocutter Document, or in any other suitable manner. As another example, two-phase deployment may be used to deploy one or more staples 4. One or more wedges 20 or other deployment mechanisms may slide relative to one or more of the staples 4 in a first pass generally along one longitudinal direction. During the first pass, the one or more wedges 20 may deploy one or more staples 4 in part or in full. Those wedges 20 or other deployment mechanisms then may slide relative to one or more of the staples 4 in a second pass generally along the opposite longitudinal direction. During the second pass, the one or more wedges 20 may complete the deployment of any partially-deployed staples 4. Alternately, the first pass of the wedges 20 deforms the staples 4, and the second pass of the wedges shears the staples 4 from the feeder belt 2.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus for treating tissues, the surgical apparatus comprising a shaft and an end effector attached to the shaft, the end effector comprising a staple holder and an anvil, the surgical apparatus further comprising a feeder belt extending into the staple holder, the feeder belt carrying a plurality of staples frangibly connected to feeder belt, each of the plurality of staples having a free end and an end frangibly connected to the feeder belt, the anvil comprising an inner surface oriented toward the staple holder, the inner surface defining a plurality of staple forming pockets, the plurality of staple forming pockets and plurality of staples being arranged such that, during deployment of the plurality of staples, the free end of each staple contacts the anvil in one of the plurality of staple forming pockets to close the staple in one of a variety of tightnesses without causing interference between the free end of each staple and a remainder of each staple as the free end is bent past the remainder of each staple.

2. The surgical apparatus of claim 1, wherein the plurality of staple forming pockets are homogeneous.

3. The surgical apparatus of claim 1, wherein the plurality of staple forming pockets extend the same distance into the inner surface.

4. The surgical apparatus of claim 1, wherein the plurality of staple forming pockets have the same shape.

5. The surgical apparatus of claim 1, wherein the plurality of staple forming pockets are non-homogeneous.

6. The surgical apparatus of claim 5, wherein the plurality of staple forming pockets extend different distances into the inner surface.

7. The surgical apparatus of claim 6, wherein the plurality of staple forming pockets comprise one or more staple forming pockets that extend a first distance into the inner surface, and one or more staple forming pockets that extend a second distance into the inner surface, the second distance being less than the first distance.

8. The surgical apparatus of claim 7, wherein the plurality of staple forming pockets further comprise one or more staple forming pockets that extend a third distance into the inner surface, the third distance being less than the second distance.

9. The surgical apparatus of claim 1, wherein each of the plurality of staple forming pockets comprises a curvature.

10. The surgical apparatus of claim 9, wherein the curvature of each of the plurality of staple forming pockets is uniform.

11. The surgical apparatus of claim 9, wherein the curvature of each of the plurality of staple forming pockets is non-uniform.

12. The surgical apparatus of claim 11, wherein the plurality of staple forming pockets comprise one or more staple forming pockets having a first radius of curvature and one or more staple forming pockets having a second radius of curvature that is less than the first radius of curvature.

13. The surgical apparatus of claim 1, wherein the plurality of staples comprise homogeneous staples.

14. The surgical apparatus of claim 1, wherein the plurality of staples comprise non-homogeneous staples.

15. The surgical apparatus of claim 1, wherein the inner surface of the anvil is flat.

16. The surgical apparatus of claim 1, wherein at least one staple includes a notch at or near the end of the at least one staple that is frangibly connected to the feeder belt, the notch reducing a thickness of the at least one staple such that the free end of the at least one staple can travel within the notch as the at one staple is closed whereby the free end does not collide with and interfere with the at least one staple at or near the end of the at least one staple.

17. The surgical apparatus of claim 1, wherein at least one staple is curved laterally whereby contact between the free end of the at least one staple and a staple forming pocket causes the free end of the at least one staple to move laterally and swipe past the end of the at least one staple that is frangibly connected to the feeder belt as the at least one staple is closed as a result of the curved lateral shape of the at least one staple.

18. The surgical apparatus of claim 1, wherein a shape of at least one staple forming pocket actively deflects the free end of the at least one staple laterally as the at least one staple is closed, thereby allowing the free end of the at least one staple to swipe past the end of the at least one staple that is frangibly connected to the feeder belt as a result of the shape of the at least one staple forming pocket.

19. The surgical apparatus of claim 1, wherein at least one of the free end of the at least one staple or a remainder of the at least one staple is shaped whereby contact between the free end of the at least one staple and the remainder of the at least one staple causes the free end of the at least one staple to deflect laterally and to prevent interference between the free end of the at least one staple and the remainder of the at least one staple as the at least one staple is closed.

20. The surgical apparatus of claim 19, wherein at least one of the free end of the at least one staple or a remainder of the at least one staple is conical or curved.

* * * * *